(12) United States Patent
Nabutovsky et al.

(10) Patent No.: US 8,647,675 B2
(45) Date of Patent: Feb. 11, 2014

(54) SILVER NANOPARTICLE ANTIMICROBIAL COATING FOR LONG-TERM AND SHORT-TERM INFECTION RESISTANCE

(75) Inventors: Yelena Nabutovsky, Sunnyvale, CA (US); Gene A. Bornzin, Simi Valley, CA (US); Annapurna Karicherla, Valencia, CA (US); Nirav Dalal, Porter Ranch, CA (US); Prashant Dinesh, Bangalore (IN); Richard Samade, Northridge, CA (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 51 days.

(21) Appl. No.: 13/415,747

(22) Filed: Mar. 8, 2012

(65) Prior Publication Data
US 2013/0238085 A1 Sep. 12, 2013

(51) Int. Cl.
*A61K 9/14* (2006.01)
*A01N 55/02* (2006.01)

(52) U.S. Cl.
USPC .......................................... 424/489; 514/494

(58) Field of Classification Search
None
See application file for complete search history.

(56) References Cited

U.S. PATENT DOCUMENTS

| 7,378,156 | B2 | 5/2008 | Terry |
| 2003/0049300 | A1 | 3/2003 | Terry |
| 2004/0116551 | A1 | 6/2004 | Terry |
| 2008/0063693 | A1 | 3/2008 | Cook et al. |
| 2008/0199536 | A1 | 8/2008 | Terry |
| 2009/0198343 | A1 | 8/2009 | Spain et al. |

FOREIGN PATENT DOCUMENTS

| EP | 0641224 B1 | 8/1998 |
| WO | 9323092 | 11/1993 |
| WO | 2005107455 A2 | 11/2005 |
| WO | 2007000591 A2 | 1/2007 |
| WO | 2007000591 A3 | 3/2007 |
| WO | 2005107455 A3 | 7/2007 |
| WO | 2007087269 A2 | 8/2007 |
| WO | 2007087269 A3 | 10/2007 |
| WO | 2010014417 A2 | 2/2010 |
| WO | 2010014417 A3 | 4/2010 |
| WO | 2010068985 A1 | 6/2010 |

OTHER PUBLICATIONS

Furna et al, "Silver Nanoparticles and Polymeric Medical Devices: A NEw Approach to Prevention of Infection?", Journal of Antimicrobial Chemotherapy, vol. 64, Issue 6, pp. 1019-1024 (Sep. 2004).*
http://sigmaaldrich.com/materials-science/nanomaterials/silver-nanoparticles), 2013.*
Agarwal, Ankit et al., "Surfaces modified with nanometer-thick silver-impregnated polymeric films that kill bacteria but support growth of mammalian cells," Biomaterials. 2010;31(4):680-690.

(Continued)

*Primary Examiner* — Carlos Azpuru

(57) ABSTRACT

Disclosed herein is an implantable medical device including an antimicrobial layer. The antimicrobial layer may include a first distinct size of silver nanoparticles, a second distinct size of silver nanoparticles, and a third distinct size of silver nanoparticles. The antimicrobial layer extends over a surface of the implantable medical device, and, in some instances, the surface of the implantable medical device may serve as a substrate on which the antimicrobial layer is deposited.

21 Claims, 4 Drawing Sheets

(56) References Cited

OTHER PUBLICATIONS

Flores, C.Y. et al., "Spontaneous adsorption of silver nanoparticles on Ti/TiO2 surfaces. Antibacterial effect on *Pseudomonas aeruginosa*," Journal of Colloid and Interface Science. 2010;350(2):402-408.

Furno, Franck et al., "Silver nanoparticles and polymeric medical devices: a new approach to prevention of infection?" Journal of Antimicrobial Chemotherapy. 2004;54(6):1019-1024.

Hindi, Khadijah M. et al., "The antimicrobial efficacy of sustained release silver-carbene complex-loaded L-tyrosine polyphosphate nanoparticles: Characterization, in vitro and in vivo studies," Biomaterials. 2009;30(22):3771-3779.

Juan, Liao et al., "Deposition of silver nanoparticles on titanium surface for antibacterial effect," International Journal of Nanomedicine. 2010;5:261-267.

Logar, Manca et al., "In situ synthesis of Ag nanoparticles in polyelectrolyte multilayers," Nanotechnology. 2007;18: 325601 (7 pp).

Lu, Xiong et al., "Nano-Ag-loaded hydroxyapatite coatings on titanium surfaces by electrochemical deposition," J.R. Soc. Interface. 2011;8(57):529-539.

Long, Yuhua et al., "Rapid sintering of silver nanoparticles in an electrolyte solution at room temperature and its application to fabricate conductive silver films using polydopamine as adhesive layers," J Mater Chem. 2011;21:4875-4881.

Magdassi, Shlomo et al., "Triggering the Sintering of Silver Nanoparticles at Room Temperature," ACS Nano. 2010;4(4)1943-1948.

Moon, Kyoung-Sik et al., "Thermal Behavior of Silver Nanoparticles for Low-Temperature Interconnect Applications," Journal of Electronic Materials. 2005;34(2):168-175.

Roe, David et al., "Antimicrobial surface functionalization of plastic catheters by silver nanoparticles," Journal of Antimicrobial Chemotherapy. 2008;61(4):869-876.

Stevens, Kris N.J. et al., "Hydrophilic surface coatings with embedded biocidal silver nanoparticles and sodium heparin for central venous catheters," Biomaterials. 2011;32(5):1264-1269.

\* cited by examiner

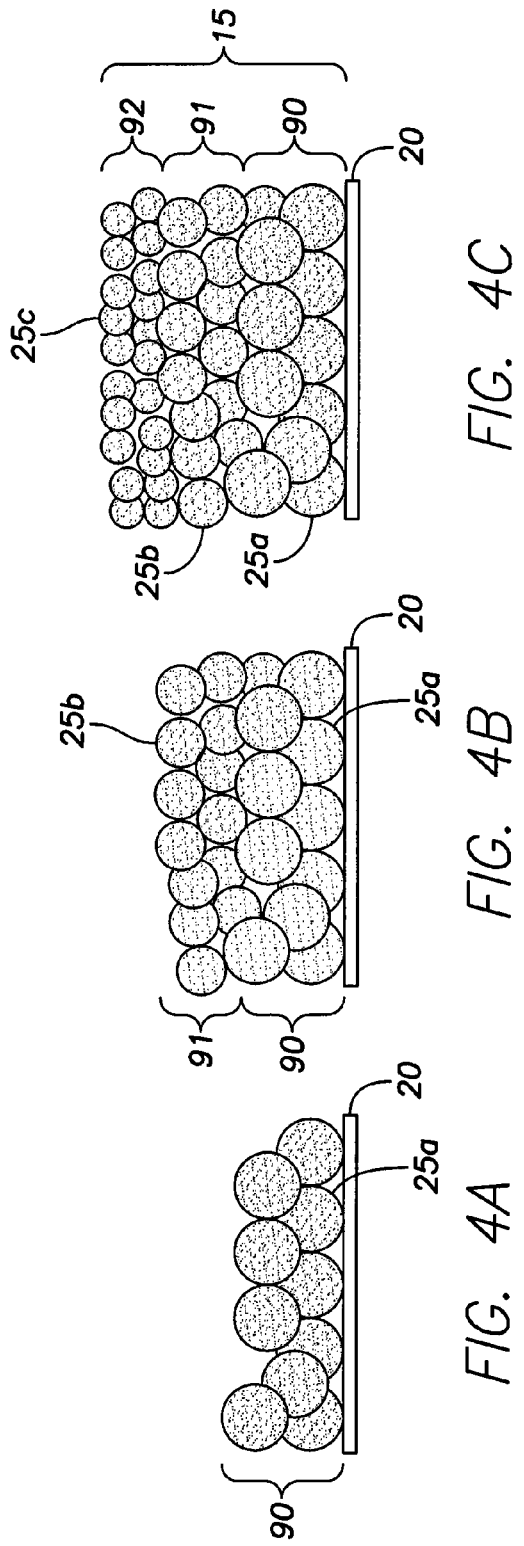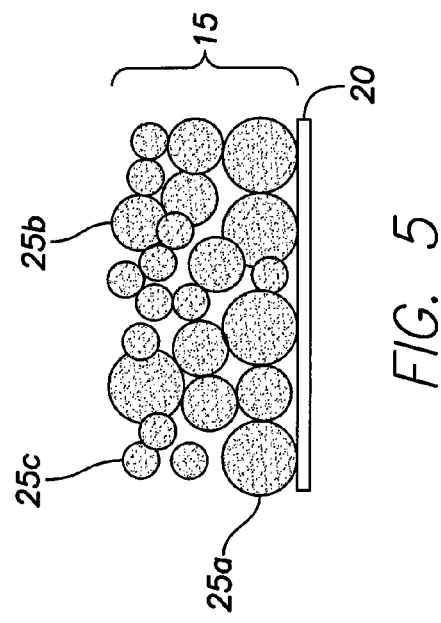

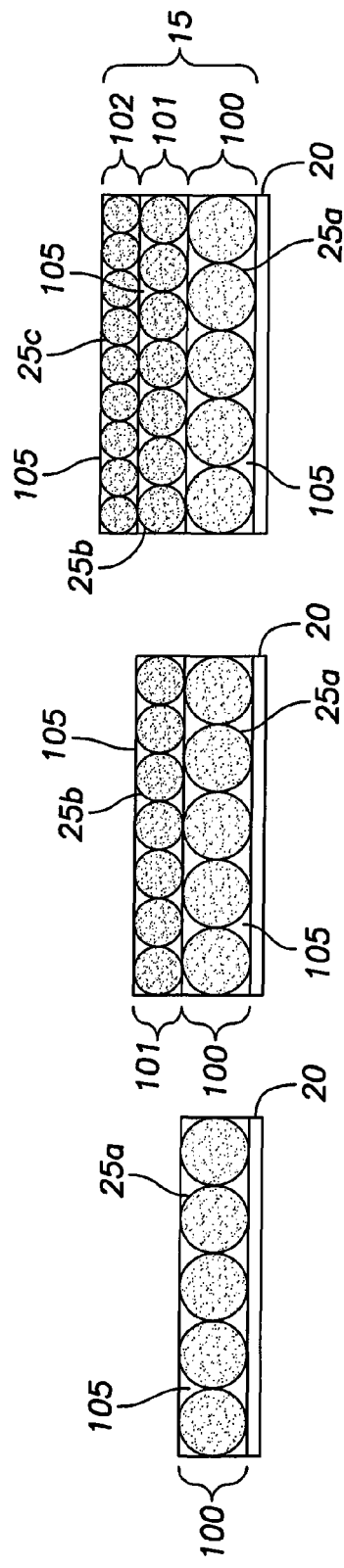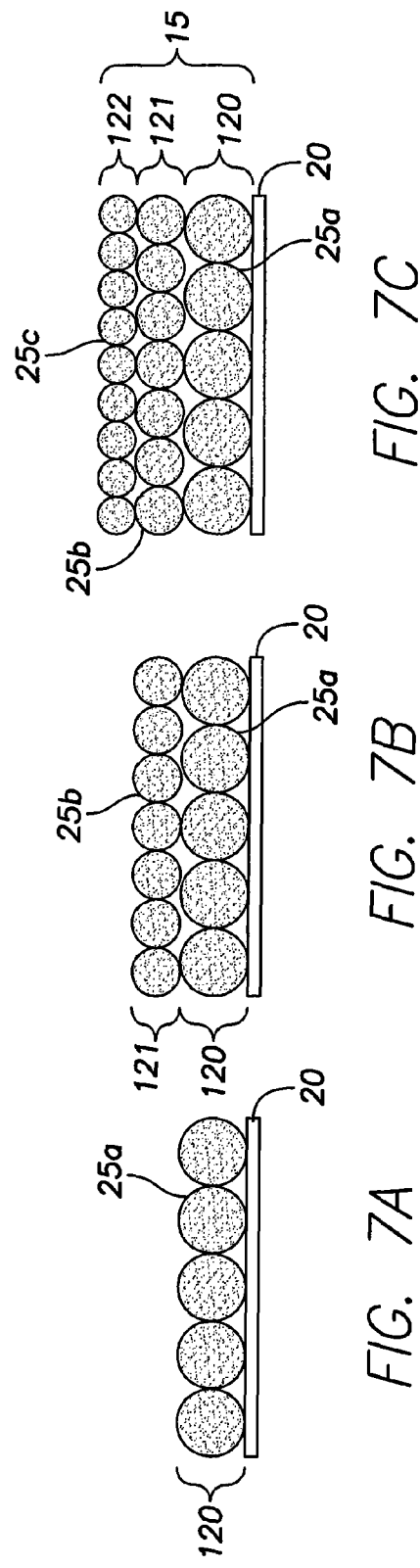

SILVER NANOPARTICLE ANTIMICROBIAL COATING FOR LONG-TERM AND SHORT-TERM INFECTION RESISTANCE

FIELD OF THE INVENTION

Aspects of the present invention relate to medical apparatus and methods. More specifically, the present invention relates to antimicrobial coatings, methods of depositing such coatings on substrates, and medical devices employing such coatings.

BACKGROUND OF THE INVENTION

Implantable device-related infection (DRI) is a serious problem that arises in about 2% of de novo implants of implantable cardioverter defibrillators (ICDs), and pacemakers. The incidence is higher for patients that are diabetic, on kidney dialysis, receiving device replacements, and undergoing lead revisions. In addition, anecdotal evidence suggests that DRIs are increasing due to growth in device complexity and are more prevalent when implanting physicians are less experienced. Similar DRI rates also occur for other types of medical device implants, including, for example, orthopedic implants, stents, catheters, etc.

A DRI is extremely costly with combined medical and surgical treatment for a DRI ranging from $25,000 to $50,000. Also, a DRI makes the patient susceptible to potentially fatal complications.

The time course of infection development is not fully understood and varies greatly. However, it has been reported that about 30 percent of infections arise less than one month post-implant, another 35 percent occur between one month and twelve months post-implant, and the remainder appear more than a year post-implant.

There is a dearth of technologies available to prevent implantable DRIs. One known product that is commercially available is the AIGIS$_{Rx}$ Anti-Bacterial Envelope, which is manufactured by TyRx Pharma, Inc. This anti-microbial pouch, designed for use with pacemakers and ICDs, is a polypropylene mesh that is shaped into a pocket and is impregnated with antibiotics. The pacemaker or ICD is placed into the AIGIS$_{Rx}$ and the covered device is subsequently implanted. The antibiotics (minocycline and rifampin) are eluted over a minimum period of 7 days in order to prevent DRIs. There are several shortcomings to this approach. First, the approach requires the implanting physician to execute an extra step of placing the pouch over the device. Second, the pouch adds bulk to the implant, which increases patient discomfort post-surgery. Third, device replacement or explant is more difficult due to growth of tissue into the mesh. Finally, the antibiotics only act for a short period of time and, as a result, do not address long-term DRIs.

There is a need in the art for a solution to both short-term and long-term DRIs that overcomes all of the above-mentioned issues.

BRIEF SUMMARY OF THE INVENTION

A first embodiment of the present disclosure may take the form of an implantable medical device including an antimicrobial layer including a first distinct size of silver nanoparticles, a second distinct size of silver nanoparticles, and a third distinct size of silver nanoparticles. The antimicrobial layer extends over a surface of the implantable medical device, and, in some instances, the surface of the implantable medical device may serve as a substrate on which the antimicrobial layer is deposited.

In one version of the first embodiment, the third distinct size of silver nanoparticles includes silver nanoparticles with a diameter of between approximately 1.5 times and approximately 2 times the diameter of the silver nanoparticles of the second distinct size of silver nanoparticles. The second distinct size of silver nanoparticles includes silver nanoparticles with a diameter of approximately 2 times the diameter of the silver nanoparticles of the first distinct size of silver nanoparticles. For example, the first distinct size of silver nanoparticles may include silver nanoparticles with a diameter of approximately 5 nm, the second distinct size of silver nanoparticles may include silver nanoparticles with a diameter of approximately 10 nm, and the third distinct size of silver nanoparticles may include silver nanoparticles with a diameter of between approximately 15 nm and approximately 20 nm.

In one version of the first embodiment, the first distinct size of silver nanoparticles are generally confined in a first sub-layer of the antimicrobial layer, the second distinct size of silver nanoparticles are generally confined in a second sub-layer of the antimicrobial layer, and the third distinct size of silver nanoparticles are generally confined in a third sub-layer of the antimicrobial layer. In versions of the first embodiment where the surface of the implantable medical device acts as a substrate for the antimicrobial layer, the third sub-layer of the antimicrobial layer may adhere directly to the substrate, the first sub-layer may form an exposed outer surface of the antimicrobial layer, and the second sub-layer may be located between the first sub-layer and the third sub-layer.

In one version of the first embodiment, the first sub-layer, second sub-layer, and third sub-layer are the products of a multi-step wet deposition process. In one version of the first embodiment, the first sub-layer, second sub-layer, and third sub-layer are the products of a multi-step PEM process. In one version of the first embodiment, the first sub-layer, second sub-layer, and third sub-layer are the products of a multi-step sintering process.

In one version of the first embodiment, the first distinct size of silver nanoparticles are confined in a polymer material forming at least part of a first sub-layer of the antimicrobial layer, the second distinct size of silver nanoparticles are confined in a polymer material forming at least part of a second sub-layer of the antimicrobial layer, and the third distinct size of silver nanoparticles are confined in a polymer material forming at least part of a third sub-layer of the antimicrobial layer. The first sub-layer, second sub-layer, and third sub-layer are the products of a multi-step polymer deposition process.

In one version of the first embodiment, the device is at least one of an implantable pulse generator or an implantable medical lead. In another version of the first embodiment, the device is at least one of an implantable medical stent or an implantable arthroplasty implant.

A second embodiment of the present disclosure may take the form of a method of applying antimicrobial protection to an implantable medical device. In one version of the second embodiment, the method includes applying an antimicrobial layer to a surface of the implantable medical device, the antimicrobial layer including multiple distinct sizes of silver nanoparticles.

In one version of the second embodiment, the multiple distinct sizes of silver nanoparticles includes a first, second and third distinct sizes of silver nanoparticles. The third distinct size of silver nanoparticles may include silver nanoparticles with a diameter of between approximately 1.5 times and approximately 2 times the diameter of the silver nanoparticles of the second distinct size of silver nanoparticles. The second distinct size of silver nanoparticles may include silver nanoparticles with a diameter of approximately 2 times the diameter of the silver nanoparticles of the first distinct size of silver nanoparticles. For example, the first distinct size of silver nanoparticles may include silver nanoparticles with a diameter of approximately 5 nm, the second distinct size of silver nanoparticles may include silver nanoparticles with a diameter of approximately 10 nm, and the third distinct size of silver nanoparticles may include silver nanoparticles with a diameter of between approximately 15 nm and approximately 20 nm.

In one version of the second embodiment, the method further includes causing the first distinct size of silver nanoparticles to be generally confined in a first sub-layer of the antimicrobial layer, the second distinct size of silver nanoparticles to be generally confined in a second sub-layer of the antimicrobial layer, and the third distinct size of silver nanoparticles to be generally confined in a third sub-layer of the antimicrobial layer. The surface of the implantable medical device may act as a substrate for the antimicrobial layer. Accordingly, the method may further include applying the third sub-layer of the antimicrobial layer so as to adhere directly to the substrate, applying the first sub-layer to as to form an exposed outer surface of the antimicrobial layer, and applying the second sub-layer so as to be located between the first sub-layer and the third sub-layer. The sub-layers may be applied via a multi-step wet deposition process or via a multi-step PEM process.

In another version of the second embodiment, the method may further include causing the first distinct size of silver nanoparticles to be confined in a polymer material forming at least part of a first sub-layer of the antimicrobial layer, causing the second distinct size of silver nanoparticles to be confined in a polymer material forming at least part of a second sub-layer of the antimicrobial layer, and causing the third distinct size of silver nanoparticles to be confined in a polymer material forming at least part of a third sub-layer of the antimicrobial layer. Such sub-layers may be applied via a multi-step polymer deposition process or a multi-step sintering process.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIGS. 4A-4C, are cross sectional elevations of the substrate with the antimicrobial coating progressively being constructed thereon.

FIG. 5 is a cross sectional elevation of another embodiment of the antimicrobial coating.

FIGS. 6A-6C are cross sectional elevations of the substrate with the coating progressively being constructed thereon via the successive application of polymer layers impregnated with nanoparticles.

FIGS. 7A-7C are cross sectional elevations of the substrate with the coating progressively being constructed thereon via a three-step polyelectrolyte multilayer (PEM) process.

DETAILED DESCRIPTION

Figure 1:
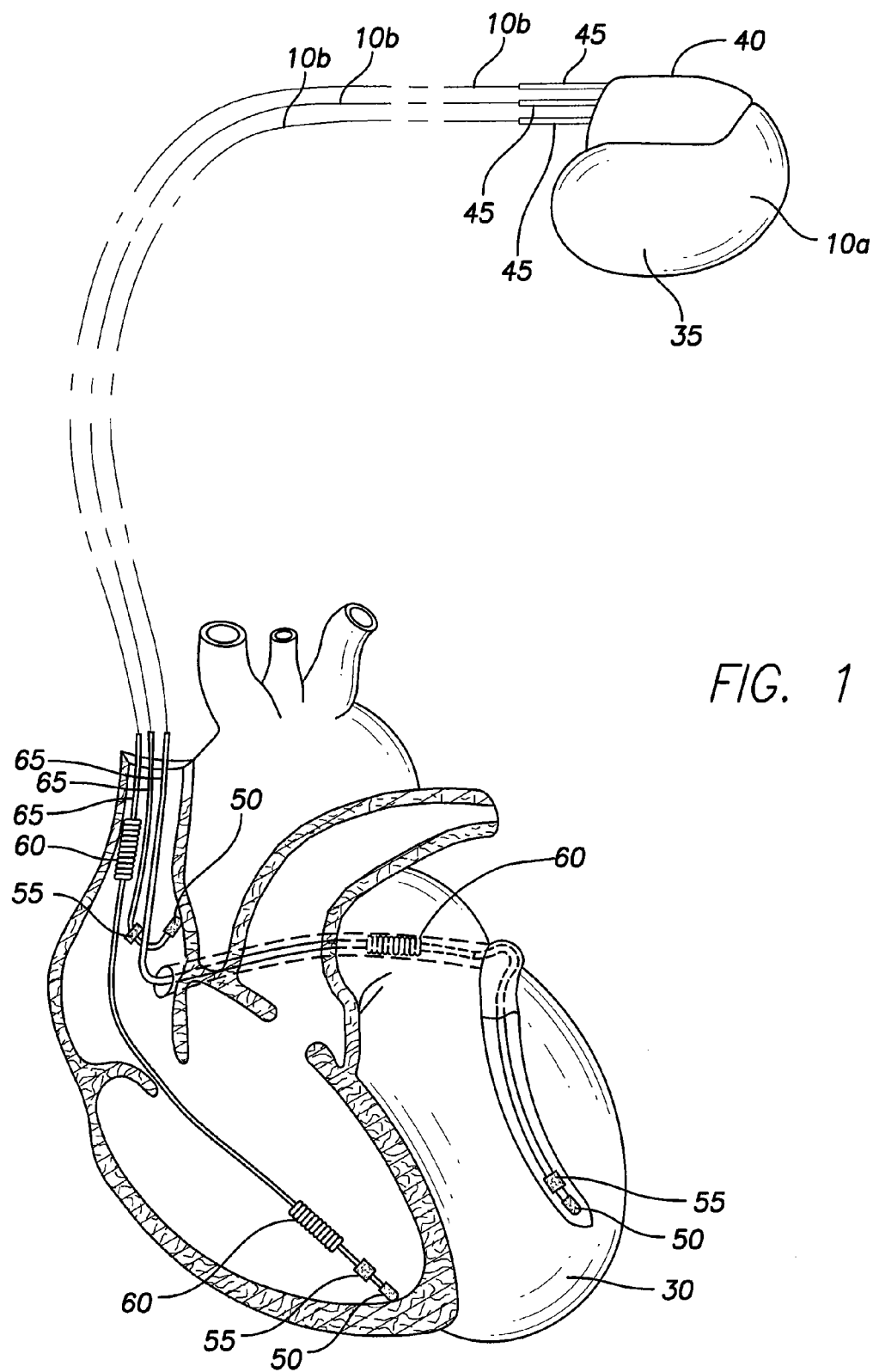
FIG. 1 is a schematic depiction of an implantable pulse generator (e.g., pacemaker, implantable cardioverter defibrillator (ICD), or etc.) electrically coupled to a patient heart via a plurality of implantable medical leads.

Implementations of the present disclosure involve implantable medical devices 10a, 10b, 10c and 10d having an antimicrobial coating 15 over an exterior substrate surface 20 of the devices, wherein the antimicrobial coating 15 includes silver nanoparticles 25a, 25b and 25c of various sizes. For example, the antimicrobial coating 15 may have silver nanoparticles 25a-25c of three generally distinct sizes, the silver nanoparticles 25a-25c serving as an antimicrobial coating 15 for the implantable medical devices 10a-10d. The size of a nanoparticle of the coating 15 determines how fast the nanoparticle will oxidize and dissolve, perform its antimicrobial function, and be excreted from the body. The smallest nanoparticles 25c of the antimicrobial coating 15 will oxidize over the course of a few days following implantation of an implantable medical device employing the coating 15, while the largest nanoparticles 25a will oxidize over a longer period of time. In some embodiments, the number of smallest nanoparticles 25c will be significantly greater than the number of large nanoparticles 25a or intermediate nanoparticles 25b.

Since most bacteria are introduced at the time of the implantation of an implantable medical device, the smallest nanoparticles 25c will provide most of the rigorous antimicrobial treatment during and immediately following the implantation. The bacteria that are introduced later will then be combated by the intermediate nanoparticles 25b, which are next to oxidize after the smallest nanoparticles 25c. The bacteria that are introduced the latest will be combated by the largest nanoparticles 25a, which are the last to oxidize. Thus, the antimicrobial coating 15 is configured to address bacteria that are introduced over an extended period.

To begin a general, non-limiting discussion regarding some of the many types of implantable medical devices that are candidates for the antimicrobial coating 15 disclosed herein, reference is made to FIG. 1, which is a schematic depiction of an implantable pulse generator (e.g., pacemaker, implantable cardioverter defibrillator (ICD), or etc.) 10a electrically coupled to a patient heart 30 via a plurality of implantable medical leads 10b. As can be shown from FIG. 1, the implantable pulse generator 10a includes a housing or can 35 in which the electronic components of the pulse generator 10a are hermetically sealed. The pulse generator 10a also includes a header 40 that receives therein the lead connector ends 45 of the respective leads 10b to mechanically couple the leads 10b to the pulse generator 10a and to electrically connect the electrical circuitry of the leads to the electrical circuitry of the pulse generator. In one embodiment, the pulse generator 10a is an implantable medical device having some or all of its exterior surfaces employing the antimicrobial coating 15 disclosed herein. For example, the exterior surfaces of the header 40 and can 35, as well as any other exterior surfaces of the pulse generator 10a, may be the substrate 20 on which the antimicrobial coating 15 is supported, as described in detail below.

In addition to the lead connector ends 45 on their respective proximal ends, each lead 10b may also have tip electrodes 50, ring electrodes 55 and shock coils 60 supported on the lead tubular body 65 near the distal end of the lead 10b. The tip and ring electrodes may be configured to pace and/or sense, and the shock coil may be configured to administer defibrillation shocks. In one embodiment, the implantable medical lead 10b is an implantable medical device having some or all its exterior surfaces employing the antimicrobial coating 15 disclosed herein. For example, any one or more or all of the exterior surfaces of the entire lead 10b and its components 45, 50, 55, 60 and 65 may be the substrate 20 on which the antimicrobial coating 15 is supported, as described in detail below.

Figure 2:
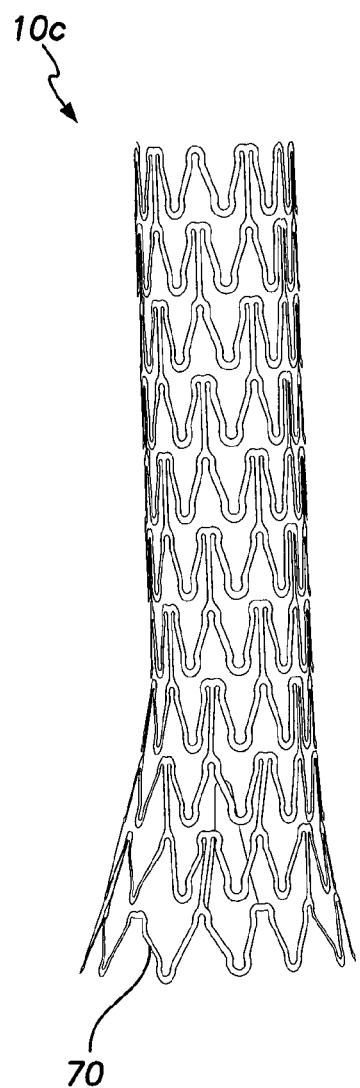
FIG. 2 is an isometric view of a self-expanding implantable medical stent.

The antimicrobial coating 15 may be employed with other implantable medical devices. For example, as can be understood from FIG. 2, which is an isometric view of an implantable self-expanding medical stent 10c, the wires or structural members 70 of the stent 10c may be coated with the antimicrobial coating 15 disclosed herein. Specifically, any one or more or all of the exterior surfaces of the entire stent 10c and its components 70 may be the substrate 20 on which the antimicrobial coating 15 is supported, as described in detail below.

Figure 3:
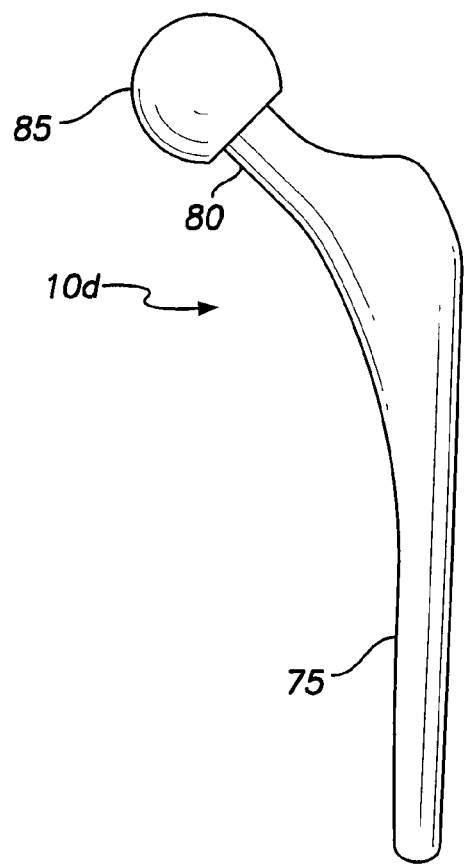
FIG. 3 is plan view of a total hip arthroplasty implant for implantation in the proximal end of a patient's femur.

The antimicrobial coating 15 may be employed with yet other implantable medical devices. For example, as can be understood from FIG. 3, which is plan view of a total hip arthroplasty implant 10d for implantation in the proximal end of a patient's femur, the intra-medullary shaft 75, neck 80 and head 85 of the hip implant 10d may be coated with the antimicrobial coating 15 disclosed herein. Specifically, any one or more or all of the exterior surfaces of the entire hip implant 10d and its components 75, 80 and 85 may be the substrate 20 on which the antimicrobial coating 15 is supported, as described in detail below.

While the preceding examples of a medical device implant employing the antimicrobial coating 15 disclosed herein are given in the context of a pulse generator 10a, an implantable medical lead 10b, a self-expanding stent 10c, and a total hip arthroplasty implant 10d. In other embodiments, the medical device implant employing the antimicrobial coating 15 disclosed herein is any type of implant now in existence or yet to come into existence, wherein the implant is intended for implantation in a patient. Accordingly, the antimicrobial coating equipped implant disclosed herein should not be limited to the four examples given with respect to FIGS. 1-3, but should be deemed to encompass all medical device implants with exterior surfaces capable of serving as substrates 20 for the antimicrobial coatings 15 disclosed herein.

To begin a discussion of one embodiment of the antimicrobial coating 15 employed on the exterior substrate surfaces 20 of the implantable medical devices such as those described above, reference is made to FIGS. 4A-4C, which are cross sectional elevations of the substrate 20 with the coating 15 progressively being constructed thereon via wet deposition. As illustrated in FIG. 4C, the antimicrobial coating 15 includes multiple layers 90, 91, 92 deposited in a stacked arrangement upon the substrate 20, which is an exterior surface of an implantable medical device such as those described above with respect to FIGS. 1-3. The innermost layer 90 (i.e., the layer extending along the outer surface of the substrate 20) is substantially, if not entirely, formed of the largest nanoparticles 25a. The outermost layer 92 (i.e., the layer forming the exterior surface of the coating 15 and on the opposite side of the coating 15 from the substrate 20) is substantially, if not entirely, formed of the smallest nanoparticles 25c. The middle layer 91 (i.e., the layer sandwiched between the innermost layer 90 and the outermost layer 92) is substantially, if not entirely, formed of medium nanoparticles 25a.

In one embodiment of the antimicrobial coating 15 depicted in FIG. 4C, the largest nanoparticles 25a are between approximately 15 nm and approximately 20 nm in diameter, the medium nanoparticles 25b are approximately 10 nm in diameter, and the smallest nanoparticles 25c are approximately 5 nm in diameter.

As can be understood from FIGS. 4A-4C, in one embodiment, the nanoparticles 25a-25c are coated directly onto the substrate 20 using a wet deposition method (e.g., immersion in a silver nanoparticle solution). Such an application of the layers 90-92 may be performed in several successive stages. For example, as indicated in FIG. 4A, in a first stage, the innermost layer 90 is applied directly to the substrate 20 by dipping the substrate 20 in a solution containing the large nanoparticles 25a substantially or exclusively. As indicated in FIG. 4B, in the second stage subsequent to the curing of the innermost layer 90 on the substrate 20, the middle layer 91 is applied to the exposed outer surface of the cured innermost layer 90 by dipping the innermost layer coated substrate 20 into a solution containing the medium nanoparticles 25b. As illustrated in FIG. 4C, in the third and final stage for a three layer coating 15 and subsequent to the curing of the middle layer 91 on the substrate 20, the outermost layer 92 is applied to the exposed outer surface of the cured middle layer 91 by dipping the middle layer coated substrate 20 into a solution containing the small nanoparticles 25c.

In some embodiments, the coating 15 depicted in FIGS. 4A-4C may have three layers 90-92, more than three layers, or as few as two layers. In such embodiments, the order of dipping should be from the largest to smallest nanoparticles, resulting in an antimicrobial coating 15 wherein the smallest nanoparticles 25c will oxidize or elute first to treat and prevent DRIs having potentially immediate onset, the medium nanoparticles 25b oxidizing or eluting next to prevent DRIs that would onset later, the large nanoparticles 25a oxidizing or eluting last to prevent DRIs that would onset still later. In this way, the smaller nanoparticles would get eluted before the larger nanoparticles.

In one embodiment of the coating 15 of FIG. 4C, the solution used to deposit the nanoparticles 25a, 25b, 25c is first comprised of water, a surfactant such as sodium saccharine, and silver nitrate. A reducing agent, such as N,N,N',N'-tetramethylethylenediamine is then added to begin the production of nanoparticles. In one embodiment, such a solution in which the substrate 20 is dipped to form the innermost layer 90 is between approximately 1% and approximately 10% by weight large silver nanoparticles 25a and the remainder of the solution is made of polymeric matrix such as polyurethane, polypyrrole, silicone, or etc. The solution containing the medium nanoparticles 25b in which the substrate 20 is dipped to form the middle layer 91 is between approximately 1% and approximately 10% by weight medium silver nanoparticles 25b and the remainder of the solution is made of polymeric matrix such as polyurethane, polypyrrole, silicone, or etc. The solution containing smallest nanoparticles 25c in which the substrate 20 is dipped to form the outermost layer 92 is between approximately 1% and approximately 10% by weight small silver nanoparticles 25c and the remainder of the solution is made of polymeric matrix such as polyurethane, polypyrrole, silicone, or etc.

A cross sectional elevation of another embodiment of the coating 15 is depicted in FIG. 5. As with the previous embodiment of the coating 15, for the coating of FIG. 5, the largest nanoparticles 25a are between approximately 15 nm and approximately 20 nm in diameter, the medium nanoparticles 25b are approximately 10 nm in diameter, and the smallest nanoparticles 25c are approximately 5 nm in diameter. The nanoparticles 25a-25c are deposited directly onto the substrate 20 using a wet deposition method (e.g., immersion in a silver nanoparticle solution) employing a single solution. Specifically, all the sizes of nanoparticles 25a-25c in the appropriate size proportions are present in solution, and the substrate 20 is dipped once into that solution. In a variation of the embodiment depicted in FIG. 5, the substrate is dipped and allowed to cure before being dipped again in the same solution. Unlike the embodiment depicted in FIG. 4C, wherein the sizes of nanoparticles 25a-25c each occupy a respective layer 90-92 of the coating 15, the layers 90-92 being arranged such that the layers 90-92 are located moving outwardly from large nanoparticle layer 90 to medium nanoparticle layer 91 to small nanoparticle layer 92, the embodiment depicted in FIG. 5 has a single layer (or multiple layers where laid up via multiple dips) that includes each size of nanoparticle 25a-25c.

In one embodiment of the coating 15 of FIG. 5, the solution in which the substrate 20 is dipped to form the coating 15 is first comprised of water, a surfactant such as sodium saccharine, and silver nitrate. A reducing agent, such as N,N,N',N'-tetramethylethylenediamine, is then added to begin the production of nanoparticles. In one embodiment of the coating 15 of FIG. 5, the solution in which the substrate 20 is dipped to form the coating 15 is between approximately 1% and approximately 10% by weight large silver nanoparticles 25a, between approximately 1% and approximately 10% by weight medium silver nanoparticles 25b, and between approximately 1% and approximately 10% by weight small silver nanoparticles 25c, the remainder of the solution being made of water, a surfactant such as sodium saccharine, and any silver nitrate that has not been reduced into nanoparticles.

To begin a discussion of another embodiment of the antimicrobial coating 15 employed on the exterior substrate surfaces 20 of the implantable medical devices such as those described above, reference is made to FIGS. 6A-6C, which are cross sectional elevations of the substrate 20 with the coating 15 progressively being constructed thereon via the successive application of polymer layers 100, 101, 102 impregnated with nanoparticles 25-a-25c. As illustrated in FIG. 6C, the antimicrobial coating 15 includes multiple polymer layers 100, 101, 102 deposited in a stacked arrangement upon the substrate 20, which is an exterior surface of an implantable medical device such as those described above with respect to FIGS. 1-3. The innermost polymer layer 100 (i.e., the layer extending along the outer surface of the substrate 20) is impregnated with nanoparticles that are substantially, if not entirely, the largest nanoparticles 25a. The outermost polymer layer 102 (i.e., the layer forming the exterior surface of the coating 15 and on the opposite side of the coating 15 from the substrate 20) is impregnated with nanoparticles that are substantially, if not entirely, the smallest nanoparticles 25c. The middle polymer layer 101 (i.e., the layer sandwiched between the innermost layer 100 and the outermost layer 102) is impregnated substantially, if not entirely, with the medium nanoparticles 25a.

In one embodiment of the antimicrobial coating 15 depicted in FIG. 6C, the largest nanoparticles 25a are between approximately 15 nm and approximately 20 nm in diameter, the medium nanoparticles 25b are approximately 10 nm in diameter, and the smallest nanoparticles 25c are approximately 5 nm in diameter.

Each size of nanoparticles 25a-25c is embedded in a polymer material 105 of a respective polymer layer 100-102. The multiple layers 100-102 are sandwiched together to form the coating 15, which may be in the form of a coating, adhered layer, package for containing the implantable medical device, or a member or feature attached to or adjacent to the implantable medical device. The multiple layers 100-102 may be deposited upon the substrate 20 and each other via successive applications of layers. Depending on the embodiment, any of the various methods of embedding silver nanoparticles in polymer materials described in the following three publications can be employed: (1) Furno F, Morley K S, Wong B, Sharp B L, Arnold P L, Howdle S M, Bayston R, Brown P D, Winship P D, Reid H J. Silver nanoparticles and polymeric medical devices: a new approach to prevention of infection? *The Journal of antimicrobial chemotherapy*. December 2004; 54(6):1019-1024; (2) Stevens K N J, Croes S, Boersma R S, Stobberingh E E, van der Marel C, van der Veen F H, Knetsch M L W, Koole L H. Hydrophilic surface coatings with embedded biocidal silver nanoparticles and sodium heparin for central venous catheters. *Biomaterials*. 2011; 32(5):1264-1269; and (3) Hindi K M, Ditto A J, Panzner M J, Medvetz D A, Han D S, Hovis C E, Hilliard J K, Taylor J B, Yun Y H, Cannon C L, Youngs W J. The antimicrobial efficacy of sustained release silver-carbene complex-loaded I-tyrosine polyphosphate nanoparticles: Characterization, in vitro and in vivo studies. *Biomaterials*. 2009; 30(22):3771-3779. These three publications are incorporated by reference herein in their entireties. The methods disclosed in the three incorporated publications lead to a polymer that contains a homogenous distribution of silver nanoparticles.

As can be understood from FIGS. 6A-6C, several layers 100-102 of polymer material 105 can be used, each layer 100-102 containing nanoparticles 25a-25c of a different specific size. In one embodiment, the outermost layer 102 is biodegradable or bioabsorbable and contains the smallest nanoparticles 25c so that once the small nanoparticles are oxidized, the polymer material 105 would dissolve exposing the next layer 101. This next layer 101, which is the middle layer 101 containing the slightly larger medium nanoparticles 25b, is also biodegradable or bioabsorbable so that once the medium nanoparticles 25b are oxidized, the polymer material 105 would dissolve exposing the next layer 100. This next layer 100, which is the innermost layer 100, may not be biodegradable. As a result, the largest nanoparticles 25a, which occupy the polymer material 105 of the innermost layer 100, would remain for a longer period of time to provide long term antimicrobial protection.

In one embodiment of the coating of FIG. 6C, the polymer material 105 of the outermost layer 102 and middle layer 101 is a biodegradable or bioabsorbable polymer such as one of synthetic materials poly(L-lactic acid), polycaprolactone, poly(lactide-co-glycolide), poly(ethylene-vinyl acetate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters), polyalkylene oxalates, polyphosphazenes, and polyarylates. The polymer material 105 of the outermost layer 102 and middle layer 101 can also be a natural material such as fibrin, fibrinogen, cellulose, starch, collagen, and hyaluronic acid, or etc. In one embodiment, the polymer material 105 of the innermost layer 100 is a non-biodegradable polymer such as silicone, polyamine, polystyrene, polyurethane, acrelate, polysilane, polysulfone, methoxysilane, or etc.

In one embodiment of the coating 15 of FIG. 6C, the polymer material containing the largest nanoparticles 25a and therewith forming the innermost layer 100 is between approximately 1% and approximately 10% by weight large silver nanoparticles 25a and the remainder of the layer 100 is made of the polymer material. The polymer material containing the medium nanoparticles 25b and therewith forming the middle layer 101 is between approximately 1% and approximately 5% by weight medium silver nanoparticles 25b and the remainder of the layer 101 is made of the polymer material. The polymer material containing the smallest nanoparticles 25c and therewith forming the outermost layer 102 is between approximately 1% and approximately 2.5% by weight small silver nanoparticles 25c and the remainder of the layer 102 is made of the polymer material.

In some embodiments, the coating 15 depicted in FIGS. 6A-6C may have three layers 100-102, more than three layers, or as few as two layers. In such embodiments, the order of successive application of the layers 100-102 should be from the largest to smallest nanoparticles, resulting in an antimicrobial coating 15 wherein the smallest nanoparticles 25c will oxidize or elute first to treat and prevent DRIs having potentially immediate onset, the medium nanoparticles 25b oxidizing or eluting next to prevent DRIs that would onset later, the large nanoparticles 25a oxidizing or eluting last to prevent DRIs that would onset still later. In this way, the smaller nanoparticles would get eluted before the larger nanoparticles.

To begin a discussion of yet another embodiment of the antimicrobial coating 15 employed on the exterior substrate surfaces 20 of the implantable medical devices such as those described above, reference is made to FIGS. 7A-7C, which are cross sectional elevations of the substrate 20 with the coating 15 progressively being constructed thereon via a three-step polyelectrolyte multilayer (PEM) process. As illustrated in FIG. 7C, the antimicrobial coating 15 includes multiple layers 120, 121, 122 deposited in a stacked arrangement upon the substrate 20, which is an exterior surface of an implantable medical device such as those described above with respect to FIGS. 1-3. The innermost layer 120 (i.e., the layer extending along the outer surface of the substrate 20) is substantially, if not entirely, formed of the largest nanoparticles 25a. The outermost layer 122 (i.e., the layer forming the exterior surface of the coating 15 and on the opposite side of the coating 15 from the substrate 20) is substantially, if not entirely, formed of the smallest nanoparticles 25c. The middle layer 121 (i.e., the layer sandwiched between the innermost layer 120 and the outermost layer 122) is substantially, if not entirely, formed of medium nanoparticles 25a.

In one embodiment of the antimicrobial coating 15 depicted in FIG. 6C, the largest nanoparticles 25a are between approximately 15 nm and approximately 20 nm in diameter, the medium nanoparticles 25b are approximately 10 nm in diameter, and the smallest nanoparticles 25c are approximately 5 nm in diameter.

As can be understood from FIGS. 7A-7C, the different sizes of nanoparticles 25a-25c are assembled into polyelectrolyte multilayers (PEMs) using one of methods described in the two following publications: (1) Agarwal A, Weis T L, Schurr M J, Faith N G, Czuprynski C J, McAnulty J F, Murphy C J, Abbott N L. Surfaces modified with nanometer-thick silver-impregnated polymeric films that kill bacteria but support growth of mammalian cells. *Biomaterials.* February 2010; 31(4):680-690; and (2) Logar M, Jancar B, Suvorov D, Kostanjsek R. In situ synthesis of Ag nanoparticles in polyelectrolyte multilayers. *Nanotechnology.* 2007; 18:1-7. These two publications are incorporated by reference herein in their entireties.

These two PEM methods involve deposition of oppositely charged polyelectrolytes on substrates where the electrostatic interaction between the two components is the driving force for the multilayer buildup. Upon the absorption of a polyca-tion onto the negatively charged substrates, the negative charges of the substrate are reversed to positive, favoring the subsequent adsorption of polyanions. This process can be repeated several times, depending on the desired number of layers and desired final structure thickness. Thus, as can be understood from FIG. 7A-7C, the layers 120-122 are laid up via three successive PEM operations.

In one embodiment, polyallylamine multilayer films of silver nanoparticles can be created using the PEM method. The PEM is built by alternately dipping the substrate in a positively charged polyelectrolyte (PAH) and a negatively charged polyelectrolyte (PAA). Once the PEM is built, the substrate with the PEM is dipped into a solution of silver nitrate, deionized water, and a reducing agent such as sodium borohydride ($NaBH_4$) to begin the formation of silver nanoparticles within the PEM. The size of the particles and their distribution can be controlled by altering the PEM assembly conditions. Specifically, the average diameter of the nanoparticles increases with increasing pH of the PAA dipping solution used to build the PEM. Therefore, in creating the large nanoparticles 25a of the innermost layer 120, the PEM can be built using PAA with a high pH (e.g., a pH of between approximately 3.3 and approximately 3.7) to synthesize the large nanoparticles 25a. In creating the medium nanoparticles 25b of the middle layer 121, the PEM can be built using PAA with a medium pH (e.g., a pH of between approximately 2.8 and approximately 3.2) to synthesize the medium nanoparticles 25b. In creating the small nanoparticles 25c of the outermost layer 122, the PEM can be built using PAA with a low pH (e.g., a pH of between approximately 2.3 and approximately 2.7) to synthesize the small nanoparticles 25c.

As indicated in FIG. 7A, the first PEM layer is built on the substrate 20 using PAA with a high pH and then dipped in the silver nitrate solution to create the innermost layer 120 with its large nanoparticles 25a. After the innermost layer 120 has cured, the next PEM layer is built using PAA with a medium pH and then dipped in the silver nitrate solution to create the middle layer 121 with its medium nanoparticles 25b over the cured innermost layer 120, as shown in FIG. 7B. After the middle layer 121 has cured, the next PEM layer is built using PAA with a low pH and then dipped in the silver nitrate solution to create the outermost layer 122 with its small nanoparticles 25c over the cured middle layer 121, as illustrated in FIG. 7C. In some embodiments, the coating 15 depicted in FIGS. 7A-7C may have three layers 120-122, more than three layers, or as few as two layers.

In one embodiment, the PEM built with higher pH PAA produces lower concentrations of nanoparticles, and the PEM built with lower pH PAA produces higher concentrations of nanoparticles. Accordingly, by using the PEM method, in one embodiment, the innermost layer 120 may include lower concentrations of large nanoparticles 25a, the middle layer 121 may have higher concentrations of medium nanoparticles 25b, and the outermost layer 122 may have still higher concentrations of small nanoparticles 25c. Such an arrangement allows for larger numbers of small nanoparticles 25c to be released during and shortly following the implantation of the implantable medical device, followed by slower release of the medium nanoparticles 25b over a later time, followed by yet slower release of the large nanoparticles 25a over yet a later time.

In one embodiment of the coating 15 of FIG. 7C, the solution containing the largest nanoparticles 25a in which the substrate 20 is dipped to form the innermost layer 120 is between approximately 1% and approximately 10% by weight large silver nanoparticles 25a and the remainder of the solution is made of water, a positively charged polyelectrolyte, and a negatively charged polyelectrolyte. The solution containing the medium nanoparticles 25b in which the substrate 20 is dipped to form the middle layer 121 is between approximately 1% and approximately 10% by weight medium silver nanoparticles 25b and the remainder of the solution is made of water, a positively charged polyelectrolyte, and a negatively charged polyelectrolyte. The solution containing smallest nanoparticles 25c in which the substrate 20 is dipped to form the outermost layer 122 is between approximately 1% and approximately 10% by weight small silver nanoparticles 25c and the remainder of the solution is made of water, a positively charged polyelectrolyte, and a negatively charged polyelectrolyte In one embodiment, the silver nanoparticles 25a-25c of the above-disclosed embodiments are silver nanoparticles the same as, or similar to, the silver nanoparticles employed in the SilvaGard coating by AcryMed, Inc. In one embodiment, the silver nanoparticles 25a-25c are the same as, or similar to, those disclosed in the five following publications: (1) Furno F, Morley K S, Wong B, Sharp B L, Arnold P L, Howdle S M, Bayston R, Brown P D, Winship P D, Reid H J. Silver nanoparticles and polymeric medical devices: a new approach to prevention of infection? *The Journal of antimicrobial chemotherapy*. December 2004; 54(6):1019-1024; (2) Agarwal A, Weis T L, Schurr M J, Faith N G, Czuprynski C J, McAnulty J F, Murphy C J, Abbott N L. Surfaces modified with nanometer-thick silver-impregnated polymeric films that kill bacteria but support growth of mammalian cells. *Biomaterials*. February 31(4):680-690; (3) Flores C Y, Diaz C, Rubert A, Benitez G A, Moreno M S, Fernandez Lorenzo de Mele M A, Salvarezza R C, Schilardi P L, Vericat C. Spontaneous adsorption of silver nanoparticles on Ti/TiO2 surfaces. Antibacterial effect on *Pseudomonas aeruginosa*. *Journal of colloid and interface science*. Oct. 15, 2010; 350(2):402-408; (4) Juan L, Zhimin Z, Anchun M, Lei L, Jingchao Z. Deposition of silver nanoparticles on titanium surface for antibacterial effect. *International journal of nanomedicine*. 2010; 5:261-267; and (5) Roe D, Karandikar B, Bonn-Savage N, Gibbins B, Roullet J B. Antimicrobial surface functionalization of plastic catheters by silver nanoparticles. *The Journal of antimicrobial chemotherapy*. April 2008; 61(4):869-876.

While the embodiments discussed herein with respect to FIGS. 4A-7C depict three layer arrangements, in other embodiments, the number of layers may be more or less than three layers. Accordingly, the embodiments disclosed herein should not be limited to three-layer embodiments but should be considered to encompass multi-layer arrangements of more or less than three layers.

In one embodiment, the silver nanoparticles 25a-25c are coated directly onto the substrate 20 using a sintering process. Such a process can be used to attach to titanium, plastics and other materials and is therefore applicable to a host of implantable medical devices, including both the can of an implantable pulse generator and the body of the implantable medical leads extending from the pulse generator. In one embodiment, as explained by Shlomo Magdassi, Michael Grouchko, Oleg Berezin, Alexander Kamyshny in "Triggering the Sintering of Silver Nanoparticles at Room Temperature," *ACS Nano*, 2010, 4 (4), pp 1943-1948, which is incorporated by reference herein in its entirety, electrolytes can be used to sinter nanoparticles at room temperature in electrolyte solutions such as, for example, NaCl and MgSO4.

In another embodiment, as explained by Yuhua Long, Junjie Wu, Hao Wang, Xiaoli Zhang, Ning Zhao and Jian Xu in "Rapid sintering of silver nanoparticles in an electrolyte solution at room temperature and its application to fabricate conductive silver films using polydopamine as adhesive layers," *J. Mater. Chem.*, 2011, 21, 4875-4881, which is incorporated by reference herein in its entirety, silver can be sintered at room temperature using a negatively charged poly electrolyte to trigger a spontaneous coalescence process.

As noted by Kyoung-Sik Moon, Hai Dong, Radenka Maric, Suresh Pothukuchi, Andrew Hunt, Yi Li and C. P. Wong in "Thermal behavior of silver nanoparticles for low-temperature interconnect applications," *Journal of Electronic Materials*, Volume 34, Number 2, 168-175, which incorporated by reference herein in its entirety, sintering of silver nanoparticles takes place at 150 to 300 degrees centigrade. Very small silver particles can sinter as low as 80 degrees Centigrade.

In one embodiment, as explained by Xiong Lu, Bailin Zhang, Yingbo Wang, Xianli Zhou, Jie Weng, Shuxin Qu, Bo Feng, Fumio Watari, Yonghui Ding and Yang Leng in "Nano-Ag-loaded hydroxyapatite coatings on titanium surfaces by electrochemical deposition," *J. R. Soc. Interface,* 2010, which incorporated by reference herein in its entirety, Nanosilver particles combined with hydroxyapatite coatings can be deposited on titanium using electrochemical deposition. Hydroxyapatite is a major component of bone and tooth enamel. Such coatings have antibacterial properties.

As can be understood from the preceding discussion, there are several methods of sintering the particles: Low temperature heating 80 to 300 degrees centigrade, chemical sintering with poly electrolytes and electrolyte solutions, electrodeposition of silver with hydroxyapatite. Also, laser beams and light have been used to sinter, AC and DC currents sinter silver ink particles, and microwaves have been used. All of the methods disclosed herein are believed to ways to sinter silver and keep it on a surface.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable medical device comprising an antimicrobial layer comprising a first distinct size of silver nanoparticles and a second distinct size of silver nanoparticles, wherein the antimicrobial layer extends over a surface of the implantable medical device.

2. The device of claim 1, wherein the surface of the implantable medical device acts as a substrate for the antimicrobial layer.

3. The device of claim 1, wherein the first distinct size of silver nanoparticles are generally confined in a first sub-layer of the antimicrobial layer, and the second distinct size of silver nanoparticles are generally confined in a second sub-layer of the antimicrobial layer.

4. The device of claim 3, wherein the first sub-layer and the second sub-layer are the products of a multi-step wet deposition process.

5. The device of claim 3, wherein the first sub-layer and the second sub-layer are the products of a multi-step PEM process.

6. The device of claim 3, wherein the first sub-layer and the second sub-layer are the products of a multi-step sintering process.

7. The device of claim 1, wherein the first distinct size of silver nanoparticles are confined in a polymer material forming at least part of a first sub-layer of the antimicrobial layer, and the second distinct size of silver nanoparticles are confined in a polymer material forming at least part of a second sub-layer of the antimicrobial layer.

8. The device of claim 7, wherein the first sub-layer and the second sub-layer are the products of a multi-step polymer deposition process.

9. The device of claim 1, wherein the antimicrobial layer further comprises a third distinct size of silver nanoparticles, and wherein the first distinct size of silver nanoparticles includes silver nanoparticles with a diameter of between approximately 15 nm and approximately 20 nm, the second distinct size of silver nanoparticles includes silver nanoparticles with a diameter of approximately 10 nm, and the third distinct size of silver nanoparticles includes silver nanoparticles with a diameter of approximately 5 nm.

10. The device of claim 9, wherein the first distinct size of silver nanoparticles are generally confined in a first sub-layer of the antimicrobial layer, and the second distinct size of silver nanoparticles are generally confined in a second sub-layer of the antimicrobial layer.

11. The device of claim 10, wherein the surface of the implantable medical device acts as a substrate for the antimicrobial layer, and the first sub-layer of the antimicrobial layer extends between the substrate and the second sub-layer of the antimicrobial layer.

12. The device of claim 1, wherein the antimicrobial layer further comprises a third distinct size of silver nanoparticles, and wherein the first distinct size of silver nanoparticles includes silver nanoparticles with a diameter of approximately 5 nm, the second distinct size of silver nanoparticles includes silver nanoparticles with a diameter of approximately 10 nm, and the third distinct size of silver nanoparticles includes silver nanoparticles with a diameter of between approximately 15 nm and approximately 20 nm.

13. The device of claim 12, wherein the first distinct size of silver nanoparticles are generally confined in a first sub-layer of the antimicrobial layer, and the second distinct size of silver nanoparticles are generally confined in a second sub-layer of the antimicrobial layer.

14. The device of claim 13, wherein the first sub-layer of the antimicrobial layer forms an outer layer of the antimicrobial layer.

15. The device of claim 1, wherein the antimicrobial layer further comprises a third distinct size of silver nanoparticles.

16. The device of claim 15, wherein the third distinct size of silver nanoparticles includes silver nanoparticles with a diameter of between approximately 1.5 times and approximately 2 times the diameter of the silver nanoparticles of the second distinct size of silver nanoparticles, the second distinct size of silver nanoparticles including silver nanoparticles with a diameter of approximately 2 times the diameter of the silver nanoparticles of the first distinct size of silver nanoparticles.

17. The device of claim 16, wherein the first distinct size of silver nanoparticles includes silver nanoparticles with a diameter of approximately 5 nm, the second distinct size of silver nanoparticles includes silver nanoparticles with a diameter of approximately 10 nm, and the third distinct size of silver nanoparticles includes silver nanoparticles with a diameter of between approximately 15 nm and approximately 20 nm.

18. The device of claim 17, wherein the first distinct size of silver nanoparticles are generally confined in a first sub-layer of the antimicrobial layer, the second distinct size of silver nanoparticles are generally confined in a second sub-layer of the antimicrobial layer, and the third distinct size of silver nanoparticles are generally confined in a third sub-layer of the antimicrobial layer.

19. The device of claim 18, wherein the surface of the implantable medical device acts as a substrate for the antimicrobial layer, and the third sub-layer of the antimicrobial layer adheres directly to the substrate, the first sub-layer forms an exposed outer surface of the antimicrobial layer, and the second sub-layer is located between the first sub-layer and the third sub-layer.

20. The device of claim 1, wherein the device is at least one of an implantable pulse generator or an implantable medical lead.

21. The device of claim 1, wherein the device is at least one of an implantable medical stent or an implantable arthroplasty implant.

* * * * *